United States Patent
Lovley et al.

(10) Patent No.: US 9,273,280 B2
(45) Date of Patent: Mar. 1, 2016

(54) GEOBACTER STRAINS THAT USE ALTERNATE ORGANIC COMPOUNDS, METHODS OF MAKING, AND METHODS OF USE THEREOF

(71) Applicants: Derek R. Lovley, Leyden, MA (US); Zarath Morgan Summers, Amherst, MA (US); Shelley Annette Haveman, Lakewood, CO (US); Mounir Izallalen, Savoy, IL (US)

(72) Inventors: Derek R. Lovley, Leyden, MA (US); Zarath Morgan Summers, Amherst, MA (US); Shelley Annette Haveman, Lakewood, CO (US); Mounir Izallalen, Savoy, IL (US)

(73) Assignee: UNIVERITY OF MASSACHUSETTS, Boston, MA (US)

( * ) Notice: Subject to any disclaimer, the term of this patent is extended or adjusted under 35 U.S.C. 154(b) by 0 days.

(21) Appl. No.: 14/070,748

(22) Filed: Nov. 4, 2013

(65) Prior Publication Data

US 2014/0154727 A1    Jun. 5, 2014

Related U.S. Application Data

(60) Division of application No. 13/021,953, filed on Feb. 7, 2011, now Pat. No. 8,597,930, which is a continuation of application No. PCT/US2009/053240, filed on Aug. 8, 2009.

(60) Provisional application No. 61/087,392, filed on Aug. 8, 2008.

(51) Int. Cl.
| | |
|---|---|
| *C12Q 1/02* | (2006.01) |
| *C12N 1/20* | (2006.01) |
| *C12N 1/36* | (2006.01) |
| *H01M 8/16* | (2006.01) |
| *H01M 4/90* | (2006.01) |
| *H01M 8/18* | (2006.01) |

(52) U.S. Cl.
CPC .. *C12N 1/20* (2013.01); *C12N 1/36* (2013.01); *H01M 8/16* (2013.01); *H01M 4/90* (2013.01); *H01M 8/18* (2013.01); *Y02E 60/527* (2013.01)

(58) Field of Classification Search
None
See application file for complete search history.

(56) References Cited

PUBLICATIONS

Yul Roh et al. "Isolation and characterization of metal-reducing Thermoanaerobacter strains from deep subsurface environments of the Piceance basin, Colorado". Applied and Environmental Microbiology. Dec. 2002, vol. 68, No. 12, pp. 6013-6020.*
Caccavo et al. Applied and Environmental Microbiology. 1994, vol. 60, No. 10, pp. 3752-3759.
Bond et al. Applied and Environmental Microbiology. 2003, vol. 69, No. 3, pp. 1548-1555.
B. A. Methe et al., Genome of Geobacter sulfurreducens: Metal Reduction in Subsurface Environments, Science 302, pp. 1967-1969, Dec. 12, 2003 (and supplementary material available on line as stated in the paper).
Nevin et al. International Journal of Systematic and Evolutionary Microbiology. 2005, 55, 1667-1674.
Shelobina et al. International Journal of Systematic and Evolutionary Microbiology. 2007, 57, 126-135.
Aklujdkar et al. Abstracts of the General meeting of the American Society for Microbiology, 2007, vol. 1 07, pp. 671-672.
Budapest Restricted Certificate of Deposit for ATTC Deposits Geobacter sulfurreducens PCA: ZMS•153 PTA•10249 and Geobacter sulfurreducens PCA: ZMS•253 PTA•10250, Aug. 5, 2009.
ISR dated Apr. 1, 2010 Issued in grandparent PCT/US09/53240.

* cited by examiner

*Primary Examiner* — Vera Afremova
(74) *Attorney, Agent, or Firm* — Milstein Zhang & Wu LLC; Joseph B. Milstein

(57) ABSTRACT

In preferred embodiments, the present invention provides new isolated strains of a *Geobacter* species that are capable of using a carbon source that is selected from $C_3$ to $C_{12}$ organic compounds selected from pyruvate or metabolic precursors of pyruvate as an electron donor in metabolism and in subsequent energy production. The wild type strain of the microorganisms has been shown to be unable to use these $C_3$ to $C_{12}$ organic compounds as electron donors. The inventive strains of microorganisms are useful for improving bioremediation applications, including in situ bioremediation (including uranium bioremediation and halogenated solvent bioremediation), microbial fuel cells, power generation from small and large-scale waste facilities (e.g., biomass waste from dairy, agriculture, food processing, brewery, or vintner industries, etc.) using microbial fuel cells, and other applications of microbial fuel cells, including, but not limited to, improved electrical power supplies for environmental sensors, electronic devices, and electric vehicles.

8 Claims, 7 Drawing Sheets ously tested fuels have produced little (such as propionate) or no current. The performance of these strains engineered by the inventors is superior to that of wild type in their ability to metabolize and transfer electrons to electrodes from the $C_3$ to $C_{12}$ organic compounds.

GEOBACTER STRAINS THAT USE ALTERNATE ORGANIC COMPOUNDS, METHODS OF MAKING, AND METHODS OF USE THEREOF

CROSS-REFERENCE TO RELATED APPLICATION

This application is a divisional of co-pending U.S. patent application Ser. No. 13/021,953, filed on Feb. 7, 2011, which is a continuation of then co-pending PCT application PCT/US09/53240, filed on Aug. 8, 2009, which itself claims priority of application 61/087,392 filed on Aug. 8, 2008. The disclosures of all of the prior applications are incorporated herein by reference, and priority is claimed.

STATEMENT REGARDING FEDERALLY SPONSORED RESEARCH

Research carried out in connection with this invention was supported in part by the Department of Energy Office of Biological and Environmental Research grant DE-FCO2-02ER634469. The United States government may have certain rights in the invention.

FIELD OF THE INVENTION

The present invention relates generally to electricigenic microorganisms capable of using organic compounds as electron donors and application of these microorganisms for use. Specific embodiments relate to new *Geobacter sulfurreducens* strains capable organic compounds selected from pyruvate or $C_3$ to $C_{12}$ metabolic precursors of pyruvate as electron donors; methods of making and methods of use therefor, including use in microbial fuel cells and bioremediation applications.

BACKGROUND OF THE INVENTION

*Geobacter sulfurreducens*, a member of the family Geobacteraceae, is a gram-negative delta-proteobacteria, which is a non-fermentative obligate anaerobe. *G. sulfurreducens* has the ability to oxidize acetate completely to $CO_2$. See, e.g., Caccavo, F., Jr., D. J. Lonergan, et al. (1994). "*Geobacter sulfurreducens* sp. nov., a hydrogen- and acetate-oxidizing dissimilatory metal-reducing microorganism." Appl Environ Microbiol 60(10): 3752-9. However, Caccavo et al., in formally describing the new species, reported that wild type strain of *Geobacter sulfurreducens*, strain PCA, did not use sulfur, glucose, lactate, fumarate, propionate, butyrate, isobutryate, isovalerate, succinate, yeast extract, phenol, benzoate, ethanol, propanol, or butanol with Fe(III) as an electron donor (Table 1). The small amounts of Fe(II) produced in cultures with glucose, lactate, malate, propanol, methanol, and yeast extract were similar to those found in cultures without an electron donor and probably represent the amounts of Fe(II) produced from the small amounts of acetate in the inocula. No Fe(II) was produced with many of the electron donors tested [including pyruvate and succinate], suggesting that these compounds inhibited the ability of PCA to use the small amount of acetate in the medium. Caccavo et. al (1994), pages 3754-3755.

*Geobacter* species are highly important in bioremediation applications. For example, their ability to reduce toxic metals such as soluble uranium (VI) to insoluble uranium (IV), immobilizes the toxic agent and aids in easier removal from the contaminated site. See, e.g., Anderson, R. T., H. A. Vrionis, et al. (2003). "Stimulating the in situ activity of *Geobacter* species to remove uranium from the groundwater of a uranium-contaminated aquifer." Appl Environ Microbiol 69(10): 5884-91. The ability of *Geobacter* species to reduce toxic metals comes from the unique mechanism of the organism's respiratory pathway. Extracellular electron transport to soluble and insoluble electron acceptors is made possible by periplasmic and outer membrane c-type cytochromes as well as conductive pilli termed nanowires. See Reguera, G., K. D. McCarthy, et al. (2005). "Extracellular electron transfer via microbial nanowires." Nature 435(7045): 1098-101. Their ability to transfer electrons outside of their cells enables *Geobacter* species to reduce not only soluble uranium, but also other electron acceptors (e.g., Fe(III) and Mn(IV) oxides, elemental sulfur, nitrate, fumarate). Another application for bioremediation is that *G. sulfurreducens*' ability to reduce compounds (e.g., Fe(III)) can be coupled with the oxidation of organic contaminates such as petroleum and landfill leachate. Other *Geobacter* species (e.g., *G. lovleyi*) are capable of reductive halogenation of chlorinated solvents such as trichloroethylene (TCE) and tetrachloroethylene (PCE), which can persist as major groundwater and soil contaminants, requiring effective bioremediation. To date, any improvements made to the rate of bioremediation or to the amount of current produced are not a result of improvements or changes to the bacteria or its metabolic processes, rather to the mechanisms and techniques that scientists use to study and explore this unique organism.

Yet another application of *Geobacter* species (e.g., *G. sulfurreducens*) extracellular electron transport is an ability to transfer electrons to the surface of an electrode in a bacterial fuel cell, resulting in the production of an electrical current. See Bond, D. R. and D. R. Lovley (2003). "Electricity production by *Geobacter sulfurreducens* attached to electrodes." Appl Environ Microbiol 69(3): 1548-55.

For example, *Geobacter* species have the ability to oxidize organic compounds to carbon dioxide with electron transfer to electrodes, producing electricity. This has been shown to have practical application for powering environmental sensors and could potentially have expanded applications for powering a variety of electronic devices. Improvements in current production have been made possible by advances in fuel cell designs, and current density has improved with each consecutive design; however, power output still continues to be only small scale.

Though many applications exist for the use of *Geobacter* strains in bioremediation and energy production, limitations to these applications remain. Limitations in the development of these expanded applications is, at least in part, due to *Geobacter* species having a limited range of fuels that can be oxidized for power production, limited primarily to simple molecules such as acetate, hydrogen, and some aromatic compounds.

SUMMARY OF THE INVENTION

In preferred embodiments, the present invention provides new strains of a microorganism that are capable of using a carbon source that is selected from $C_3$ to $C_{12}$ organic compounds selected from pyruvate or metabolic precursors of pyruvate as an electron donor in metabolism and in subsequent energy production. In other aspects, other preferred embodiments of the present invention include methods of making such strains and methods of using such strains. In general, the wild type strain of the microorganisms has been shown to be unable to use these $C_3$ to $C_{12}$ organic compounds as electron donors in metabolic steps such as the reduction of metallic ions. The inventive strains of microorganisms are useful for improving bioremediation applications, including in situ bioremediation (including uranium bioremediation and halogenated solvent bioremediation), microbial fuel cells, power generation from small and large-scale waste facilities (e.g., biomass waste from dairy, agriculture, food processing, brewery, or vintner industries, etc.) using microbial fuel cells, and other applications of microbial fuel cells, including, but not limited to, improved electrical power supplies for environmental sensors, electronic devices, and electric vehicles.

The present invention provides an isolated *Geobacter* strain capable of efficient utilization of lactate as an electron donor source. In some embodiments, the isolated *Geobacter* strain is an isolated strain of *Geobacter sulfurreducens, Geobacter metallireducens, Geobacter lovleyi, Geobacter pickeringii, Geobacter grbiciae, Geobacter pelophilus, Geobacter bremensis, Geobacter hydrogenophilus, Geobacter uraniireducens, Geobacter humireducens, Geobacter bemidjiensis, Geobacter argillaceus, Geobacter chapellei, Geobacter psychrophilus, Geobacter pilgrimii, Geobacter plymouthensis, Geobacter rifilensis, Geobacter coloradoensis*, or a mixture of *Geobacter* strains. In preferred embodiments, the *Geobacter* strain is a strain of *Geobacter sulfurreducens*.

In particularly preferred embodiments, the inventive *Geobacter sulfurreducens* strains have in common a mutation in a gene encoding for a repressor of succinyl CoA synthetase activity. For example, a functional mutation that allows for expression or activation of succinyl CoA synthetase enzyme. For example, a mutation in a gene coding for a transcriptional repressor (e.g., the gene encoding GSU0514) acting on the succinyl-CoA synthetase promoter, wherein the mutation results in activation of succinyl CoA synthetase enzyme. In some embodiments, the *Geobacter* strain comprises a functional mutation in the transcriptional repressor encoded by GSU0514. In preferred embodiments, the functional mutation is produced by the change of a single nucleotide pair (SNP) in GSU0514.

In preferred embodiments, the present invention provides a *Geobacter sulfurreducens* strain that grows well in growth medium containing lactate as an electron donor, and grows relatively poorly in growth medium in which acetate replaces lactate as an electron donor. In particularly preferred embodiments, the *Geobacter sulfurreducens* strain has a single nucleotide pair (SNP) mutation of G to A at position 548250 in GSU0514 that results in an E to K change in the gene product, a repressor of succinyl-CoA synthetase, and is identified as strain ZMS-153. The *Geobacter sulfurreducens* strain ZMS-153 has been deposited, and further is identified as ATCC deposit PTA-10249.

In some embodiments, the isolated *Geobacter* strain is capable of efficient utilization of glucose effective to support growth and replication. In particularly preferred embodiments, the *Geobacter sulfurreducens* strain has a single nucleotide pair (SNP) mutation of G to A at position 548250 in GSU0514 that results in an E to K change in the gene product, a repressor of succinyl-CoA synthetase, and is identified as strain ZMS-253. The *Geobacter sulfurreducens* strain ZMS-253 has been deposited, and further is identified as ATCC deposit PTA-10250.

In other embodiments, the isolated *Geobacter* strain is capable of efficient utilization of glycerol effective to support growth and replication. In particularly preferred embodiments, the *Geobacter sulfurreducens* strain has a single nucleotide pair (SNP) mutation of G to A at position 548250 in GSU0514 that results in an E to K change in the gene product, a repressor of succinyl-CoA synthetase, and is identified as strain ZMS-353.

In some embodiments, the isolated *Geobacter* strain is capable of efficient utilization of xylose effective to support growth and replication. In particularly preferred embodiments, the *Geobacter sulfurreducens* strain has a single nucleotide pair (SNP) mutation of G to A at position 548250 in GSU0514 that results in an E to K change in the gene product, a repressor of succinyl-CoA synthetase, and is identified as strain ZMS-453.

In preferred embodiments, the invention provides an isolated *Geobacter* strain capable of effective utilization of an organic compound selected from the group consisting of pyruvate and $C_3$ to $C_{12}$ metabolic precursors of pyruvate as an electron donor, and having a functional mutation in a gene encoding a repressor of an enzyme of the tricarboxylic acid cycle. The isolated *Geobacter* strain can be an isolated strain selected from the group consisting of *Geobacter sulfurreducens, Geobacter metallireducens, Geobacter lovleyi, Geobacter pickeringii, Geobacter grbiciae, Geobacter pelophilus, Geobacter bremensis, Geobacter hydrogenophilus, Geobacter uraniireducens, Geobacter humireducens, Geobacter bemidjiensis, Geobacter argillaceus, Geobacter chapellei, Geobacter psychrophilus, Geobacter pilgrimii, Geobacter plymouthensis, Geobacter rifilensis, Geobacter coloradoensis*. In particularly preferred embodiments, the isolated *Geobacter* strain is an isolated *Geobacter sulfurreducens* strain identified as ATCC deposit PTA-10249, or PTA-10250. In other preferred embodiments, the isolated *Geobacter* strain is an isolated *Geobacter sulfurreducens* strain identified as ZMS-253, ZMS-353 or ZMS-453. In preferred embodiments, the functional mutation is in a gene encoding a transcriptional repressor acting on the succinyl-CoA synthetase promoter, wherein the mutation results in the activation of the succinyl CoA synthetase enzyme, and more preferably the functional mutation is in the gene encoding GSU0514.

In another aspect, in preferred embodiments, the invention provides a method of improving electricity production of a microbial fuel cell comprising the steps of providing a fuel cell comprising an anode connected to a cathode through a conductive connection, and further connected to a load; providing an isolated anodophilic *Geobacter* strain that can use an organic compound selected from the group consisting of pyruvate and $C_3$ to $C_{12}$ metabolic precursors of pyruvate as an electron donor; and providing the corresponding organic compound, wherein the oxidation of the organic compound by the *Geobacter* strain results in improved generation of electricity in the fuel cell. In preferred embodiments the microbial fuel cell is used to power environmental sensors, electronic devices or electric vehicles. In preferred embodiments, the isolated *Geobacter* strain is capable of effective utilization of an organic compound selected from the group consisting of pyruvate and $C_3$ to $C_{12}$ metabolic precursors of pyruvate as an electron donor, and having a functional mutation in a gene encoding a repressor of an enzyme of the tricarboxylic acid cycle.

In another aspect, in preferred embodiments, the invention provides a method of generating electrical power at a waste facility comprising the steps of providing a waste compartment enclosing an anode, the anode being connected to a cathode through a conductive connection, and further connected to a load for power generation at the waste facility; providing an isolated anodophilic *Geobacter* strain capable of effective utilization of an organic compound selected from the group consisting of pyruvate and $C_3$ to $C_{12}$ metabolic precursors of pyruvate, and adding to the waste compartment the *Geobacter* strain and a amount of a waste product located at the waste facility, the waste product comprising the selected organic compound; wherein the organic compound in the waste product is oxidized by the *Geobacter* strain, thereby, thereby generating electrical power at the waste facility. In preferred embodiments, waste facility has a waste product that includes a biomass waste resulting from any one of a dairy, agriculture, food processing, brewery, or vintner industry. In preferred embodiments, the isolated *Geobacter* strain is capable of effective utilization of an organic compound selected from the group consisting of pyruvate and $C_3$ to $C_{12}$ metabolic precursors of pyruvate as an electron donor, and having a functional mutation in a gene encoding a repressor of an enzyme of the tricarboxylic acid cycle.

In another aspect, in preferred embodiments, the invention provides a method of improving in situ bioremediation of a contaminated site comprising the steps of providing an anode and a cathode in the soil at a location in the contaminated site, where the anode and a cathode are each connected to the respect terminals of an electrical supply; adding to the soil of the location at least a sufficient amount of an organic compound selected from the group consisting of lactic acid, salts thereof, lactate esters, poly-lactate, or mixtures thereof for use as an electron donor for a contaminant found in the groundwater or soil of the location; adding an isolated *Geobacter* strain capable of effective utilization of lactate as an electron donor to the soil of the location, wherein the strain is added optionally before, after, or during the addition of the organic compound; wherein the *Geobacter* strain uses the added organic compound as an electron donor for reduction of the contaminant as the electron acceptor, thereby improving in situ bioremediation of the contaminated site. In certain embodiments, the contaminant is a halogenated solvent, and utilization of the electron donor by the *Geobacter* strain results in the dehalogenation of the halogenated solvent. In certain embodiments, the contaminant is a toxic metal or radionuclide selected from uranium, vanadium, chromium, technetium, and cobalt. In preferred embodiments, the isolated *Geobacter* strain is capable of effective utilization of an organic compound selected from the group consisting of pyruvate and $C_3$ to $C_{12}$ metabolic precursors of pyruvate as an electron donor, and having a functional mutation in a gene encoding a repressor of an enzyme of the tricarboxylic acid cycle.

In a different aspect, preferred embodiments of the present invention provide a method of making an isolated adapted strain of an electricigenic microbe that can use an alternative organic compound as an electron donor, wherein the alternative organic compound is not preferably used as an electron donor by a parent strain of the electricigenic microbe, comprising the steps of a) providing a first vessel that contains a first culture, the first culture comprising the parent strain of the electricigenic microbe, and a first growth medium that includes a preferred organic compound as an electron donor and a corresponding electron acceptor; b) inoculating a second vessel that contains a second growth medium that includes an alternative organic compound that replaces the preferred organic compound as an electron donor and a corresponding electron acceptor with an aliquot of the parent strain of the electricigenic microbe to form a adapted culture; c) monitoring a growth rate of the adapted culture, noting the start of the exponential phase, and continuing until the growth rate is in mid or late exponential phase; d) setting n=1, where n is an integer from 1 to 100, inclusive; e) n=n+1; f) transferring an aliquot of the adapted culture to another vessel that contains the second growth medium to inoculate a nth adapted culture; g) monitoring the growth rate of the nth adapted culture, noting the start of the exponential phase, and continuing until the growth rate is in mid or late exponential phase; h) repeating steps e-g unless either the time period from inoculation until the start of the exponential phase of the nth adapted culture is more than 0.4× the time period from inoculation until the start of the exponential phase of the n−1th adapted culture; or the increase in the growth rate of the nth adapted culture compared to its predecessor is less than that of the n−1 adapted culture compared to its predecessor, or the doubling time of the nth adapted culture in the second growth medium is greater than or equal to the doubling time of the parent strain in the first growth medium; and i) isolating the adapted strain of the electricigenic microbe from the nth adapted culture.

In preferred embodiments, the preferred organic compound is acetate and the alternative organic compound is pyruvate or a $C_3$ to $C_{12}$ metabolic precursor of pyruvate. In some such embodiments, typically the parent strain is the PCA strain of *Geobacter sulfurreducens* and the isolated adapted strain is *Geobacter sulfurreducens* strain 1-23 or strain ZMS-153. In certain embodiments, the preferred organic compound is acetate and the alternative organic compound is lactate.

In other preferred embodiments, the parent strain is the 1-23 strain of *Geobacter sulfurreducens*, the preferred organic compound is lactate and the alternative organic compound is glucose. In particularly preferred embodiments, the adapted strain of *Geobacter sulfurreducens* produced by these methods is the strain identified as ZMS-253.

In further preferred embodiments, the parent strain is the 1-23 strain of *Geobacter sulfurreducens*, the preferred organic compound is lactate and the alternative organic compound is glycerol. In particularly preferred embodiments, the adapted strain of *Geobacter sulfurreducens* produced by these methods is the strain identified as ZMS-353.

In yet other preferred embodiments, the parent strain is the 1-23 strain of *Geobacter sulfurreducens*, the preferred organic compound is lactate and the alternative organic compound is xylose. In particularly preferred embodiments, the adapted strain of *Geobacter sulfurreducens* produced by these methods is the strain identified as ZMS-453.

BRIEF DESCRIPTION OF THE DRAWINGS

FIG. 2). Also plotted are the changes in the concentrations of pyruvate (filled diamonds) and fumarate (filled squares) in the medium, as determined by HPLC.

DESCRIPTION OF PREFERRED EMBODIMENTS

Figure 1:
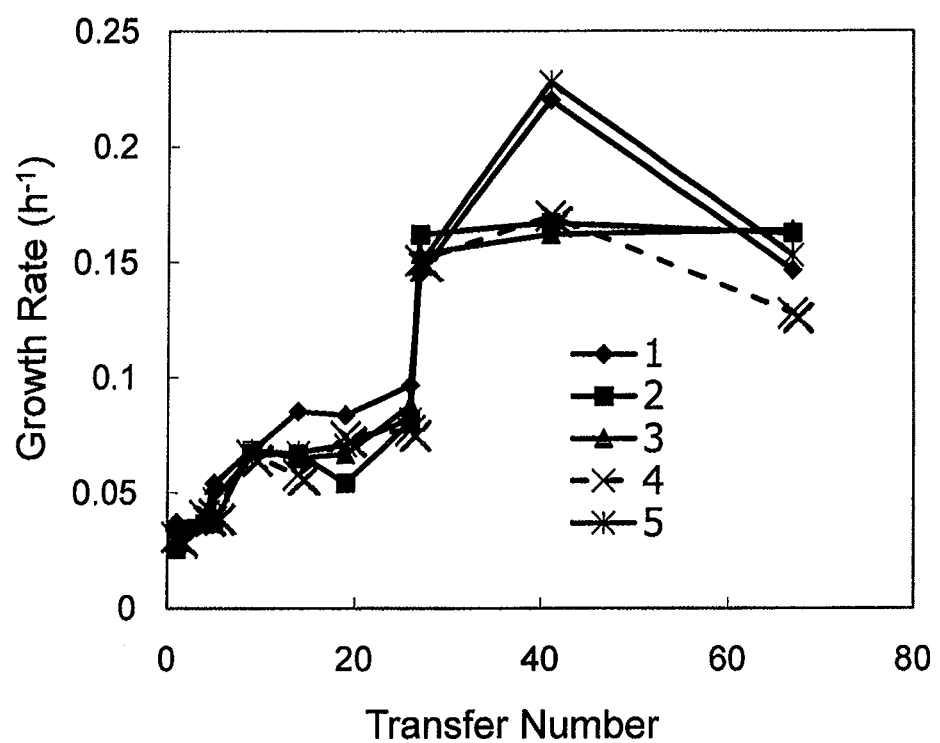
FIG. 1 depicts growth rates per hour on lactate medium of strains that were continuously passaged to produce strains that could use lactate efficiently as an electron donor. The curves represent five parallel cultures that were continuously transferred in lactate medium. The growth rate of a culture (ordinate) is plotted against the transfer number of the culture (abscissa).

A metabolic feature of *Geobacter* species of electricigenic microbes is the limited range of substrates that these organisms can metabolize. This feature limits the current production possible when using *Geobacter* species in microbial fuel cells that use complex wastes as fuel and also restrict the fuel substrates that can be used to promote in situ bioremediation using *Geobacter* species. For example, the wild-type ancestral strain of *G. sulfurreducens* has been demonstrated to be unable to use certain compounds, such as lactate, pyruvate, glucose and glycerol, as electron donors in the absence of acetate. Furthermore, although the wild-type ancestral strain of *G. sulfurreducens* can grow on lactate, its doubling time with lactate as the electron donor and fumarate as the electron acceptor is greater or equal to 24 hours, typically 24-26 hours.

A solution to the limitations imposed by this metabolic feature of *Geobacter* species is to generate new strains of *Geobacter* species that can use a broader range of organic compounds as electron donors, compounds that provide more energy that acetate. We have found that the repeated transfer of *Geobacter sulfurreducens* in lactate-fumarate medium for over 500 generations resulted in generation of a lactate adapted strain (isolate 1-23) that had a doubling time in lactate-ferric chloride growth medium of that was reduced to about 5 hours. The lactate-adapted strain not only had improved growth on lactate growth media, but could also effectively utilize pyruvate and a number of $C_3$ to $C_{12}$ metabolic precursors of pyruvate, such as glucose, glycerol and xylose for growth and as an electron donor source. In addition to the common ability to effectively utilize pyruvate and $C_3$ to $C_{12}$ metabolic precursors of pyruvate as electron donors, the inventive strains share the common technical feature of a single nucleotide pair (SNP) mutation of G to A at position 548250 in GSU0514 that results in an E to K change in the gene product, a repressor of succinyl-CoA synthetase. Genetic experiments in which this portion of the gene is "knocked-in" or "knocked-out" described below in Example 3 demonstrate that the desirable solution provided by these new strains of *Geobacter sulfurreducens*, specifically the ability to pyruvate and $C_3$ to $C_{12}$ metabolic precursors of pyruvate as electron donors is functionally linked to the mutation that is common to the inventive strains.

As used herein "effectively utilize," "effective utilization," or "effectively use" refers to the ability of a strain of microorganism to use a compound for growth and proliferation.

In preferred embodiments, the present invention provides an isolated *Geobacter* strain capable of efficient utilization at least one of pyruvate or a $C_3$ to $C_{12}$ metabolic precursor of pyruvate such as lactate, glucose, galactose, sucrose, maltose, xylose, or glycerol as an electron donor source. In certain preferred embodiments, the isolated *Geobacter* strain is a strain of *Geobacter sulfurreducens*, *Geobacter metallireducens*, *Geobacter lovleyi*, *Geobacter pickeringii*, *Geobacter grbiciae*, *Geobacter pelophilus*, *Geobacter bremensis*, *Geobacter hydrogenophilus*, *Geobacter uraniireducens*, *Geobacter humireducens*, *Geobacter bemidjiensis*, *Geobacter argillaceus*, *Geobacter chapellei*, *Geobacter psychrophilus*, or a mixture of *Geobacter* strains. In certain preferred embodiments, the isolated *Geobacter* strain is a strain of *Geobacter sulfurreducens*.

Microbial fuel cells and devices utilizing microbial fuel cells have been developed which utilize microorganisms as catalysts to provide electricity and power from oxidation of a substrate. For example, oxidation of a substrate by a microorganism results in electrons transferred to an anode, which flow to a cathode through a conductive connection. The conductive connection may then be further connected to a load (e.g., a device powered by resulting electricity produced by the fuel cell) for power generation. To date, however, applications of fuel cells are limited by an inability to provide readily available oxidation substrates in amounts sufficient to maintain operation, and, further, to maintain efficient oxidation in order to produce effective power generation.

Thus, provided are embodiments in which a *Geobacter* strain that can effectively utilize pyruvate or $C_3$ to $C_{12}$ metabolic precursors of pyruvate is used as a biocatalyst to provide electricity and power from the oxidation of the pyruvate or $C_3$ to $C_{12}$ metabolic precursors of pyruvate in a microbial fuel cell. Typically, such a microbial fuel cell includes an anode, a cathode, an electrically conductive connector connecting the anode and the cathode, a *Geobacter* strain that can effectively utilize pyruvate or $C_3$ to $C_{12}$ metabolic precursors of pyruvate, and, optionally, a cation exchange membrane. In certain embodiments, a microbial fuel cell may further comprise a fuel cell housing for containing a transfer medium, wherein the transfer medium is in contact with at least a portion of the anode, and wherein pyruvate or $C_3$ to $C_{12}$ metabolic precursors of pyruvate is disposed in the transfer medium. In certain embodiments, a *Geobacter* strain capable of effective utilization of pyruvate or $C_3$ to $C_{12}$ metabolic precursors of pyruvate is anodophilic, and capable of direct transfer of electrons to an anode. In certain embodiments, an anode is supplied wherein the anode comprises a film of the *Geobacter* strain that can effectively utilize pyruvate or $C_3$ to $C_{12}$ metabolic precursors of pyruvate. In certain embodiments, the bacterium can be anodophilic and transfer electrons through a mediator, wherein the bacteria may or may not be directly in contact with the anode. Where a mediator is required for electron transfer, such mediator may be exemplified by use of ferric oxides, neutral red, anthraquinone-1,6-disulfonic acid (ADQS) and 1,4-napthoquinone (NQ). Mediators are optionally chemically bound to an anode, or an anode modified by various treatments, such as coating, to contain one or more mediators.

In general, operation of a microbial fuel cell configured to produce electricity, a provided oxidizable substrate is oxidized by bacteria which generate electrons, protons and carbon dioxide. The electrons are transferred to the anode, and, through a load such as a device to be powered, to the cathode. Protons and electrons react with oxygen at the cathode, producing water.

A fuel of pyruvate or $C_3$ to $C_{12}$ metabolic precursors of pyruvate may be disposed in a microbial fuel cell comprising a Geobacter strain of embodiments of the present invention in a variety of manners relative to the anode, and to other components. For example, the fuel may be included in an aqueous medium in contact with an anode. In other embodiments, a microbial fuel cell configuration can include a container or package comprising the fuel, wherein the package is porous to a bacterium. In certain other embodiments, a container or package comprising the fuel is positioned in proximity to an anodophilic bacterium. In some embodiments, a container or package containing the fuel is positioned on the anode, and in proximity and/or in direct contact with the bacterium.

In certain embodiments, the fuel of a microbial fuel cell is replenishable. For example, a container comprising the fuel may be replaced upon utilization of the fuel contents. A microbial fuel cell may be configured as a self-contained fuel cell in particular embodiments. Thus, for example, a quantity of the fuel is included in the fuel cell and no additional fuel may be added. In further options, additional fuel is added at intervals or continuously such that the fuel cell operates as a batch processor or as a continuous flow system.

In preferred embodiments, the fuel in a microbial fuel cell is selected from the group consisting of pyruvate, lactate, glucose, galactose, sucrose, maltose, xylose, glycerol, and mixtures thereof.

An electrical power supply for enhancing the electrical potential between an anode and cathode of a microbial fuel cell may be included. Electrical power supplies suitable for such purposes are known, and may include, but are not limited to an electric power utility, a solar power source such as a photovoltaic device, a hydroelectric power source, a wind power source, such as a wind turbine, or an electrochemical power source such as a battery or a capacitor.

Electrodes included in a microbial fuel cell useful in the invention are electrically conductive. Exemplary conductive electrode materials include, but are not limited to, carbon paper, carbon cloth, carbon felt, carbon wool, carbon foam, graphite, porous graphite, graphite powder, a conductive polymer, a conductive metal, and combinations of any of these.

In certain embodiments, a method of improving fuel production (e.g., electricity, power generation) of a microbial fuel cell is provided. In some embodiments, the method comprises providing an anodophilic Geobacter strain capable of the effective utilization of pyruvate or $C_3$ to $C_{12}$ metabolic precursors of pyruvate, providing a fuel selected from pyruvate or $C_3$ to $C_{12}$ metabolic precursors of pyruvate, and providing a fuel cell comprising an anode connected to a cathode through a conductive connection. The conductive connection may then be further connected to a load (e.g., a device powered by resulting electricity produced by the fuel cell) for power generation. Oxidation of the fuel by the Geobacter results in generation of electricity. Further details of the construction and use of such microbial fuel cells are provided in U.S. published patent application US2008/0288624, which is incorporated herein in its entirety.

In some embodiments, a microbial fuel cell is utilized for power of environmental sensors. In other embodiments, a microbial fuel cell is utilized for power of electronic devices or electric vehicles.

In still other embodiments, provided microorganisms are useful in a method of generating power from a waste facility. In some embodiments, the method comprises providing an anodophilic Geobacter strain capable of the effective utilization of pyruvate or $C_3$ to $C_{12}$ metabolic precursors of pyruvate, providing a waste compartment comprising a fuel capable of being effectively utilized by the Geobacter strain (e.g., a waste product comprising pyruvate or $C_3$ to $C_{12}$ metabolic precursors of pyruvate), and providing to the waste compartment an anode connected to a cathode through a conductive connection, which is further connected to a load (e.g., a device powered by resulting electricity produced) for power generation. Addition of the Geobacter strain and such waste product to the compartment, and oxidation of the fuel in the waste product by the Geobacter results in generation of electricity, thereby generating power from the waste facility.

The waste facility can be any waste facility, from a small (e.g., individual or local) waste collection system to a large, industrial waste containment and/or processing facility. In some embodiments, the waste facility is biomass waste from a dairy, agriculture, food processing, brewery, or vintner industry. In other embodiments, the waste facility is a municipal waste facility, a yard waste or green waste facility, or an animal waste facility.

In certain embodiments, the present invention provides a method comprising providing a Geobacter strain capable of effective utilization of xylose, a microbial fuel cell, and a wood waste product comprising xylose as a fuel, wherein the Geobacter strain effectively utilizes the xylose in the wood waste product, resulting in the generation of electricity. The wood waste product can suitably comprise wood chips, sawdust, or yard waste. In particularly preferred embodiments, the Geobacter strain is a Geobacter sulfurreducens strain comprising a functional mutation in the transcriptional repressor encoded by GSU0514. In preferred embodiments, the functional mutation is produced by the change of a single nucleotide pair (SNP) in GSU0514. In certain preferred embodiments, the Geobacter sulfurreducens strain is ZMS-453.

In certain other embodiments, the invention provides a method including the steps of providing a Geobacter strain capable of effective utilization of glucose and a waste product comprising glucose to a microbial fuel cell, wherein the Geobacter strain effectively utilizes the glucose in the waste product, resulting in the generation of electricity. In some embodiments the glucose containing waste product comprises milk, wine, beer, or sugar production waste products. In particularly preferred embodiments, the Geobacter strain is a Geobacter sulfurreducens strain comprising a functional mutation in the transcriptional repressor encoded by GSU0514. In preferred embodiments, the functional mutation is produced by the change of a single nucleotide pair (SNP) in GSU0514. In certain preferred embodiments, the Geobacter sulfurreducens strain is ZMS-253. In particularly preferred embodiments, the Geobacter sulfurreducens strain used in the method is the strain deposited on Aug. 5, 2009, on behalf of University of Massachusetts, 225 Franklin Street, Boston, Mass. 02110, U.S.A., at the American Type Culture Collection, Patent Depository, 10801 University Boulevard, Manassas, Va. 20110, U.S.A., under Accession No. PTA-10250.

In further embodiments, the present invention provides a method comprising a providing a *Geobacter* strain capable of effective utilization of glycerol and a waste product comprising glycerol to a microbial fuel cell, wherein the *Geobacter* strain effectively utilizes the glycerol in the waste product, resulting in the generation of electricity. In some embodiments, the glycerol containing waste product comprises waste products from biodiesel production. In particularly preferred embodiments, the *Geobacter* strain is a *Geobacter sulfurreducens* strain comprising a functional mutation in the transcriptional repressor encoded by GSU0514. In preferred embodiments, the functional mutation is produced by the change of a single nucleotide pair (SNP) in GSU0514. In certain preferred embodiments, the *Geobacter sulfurreducens* strain is ZMS-353.

In other embodiments, a method of improved in situ bioremediation is provided. In some embodiments, the method comprises adding a *Geobacter* strain capable of effective utilization of a compound selected from pyruvate or $C_3$ to $C_{12}$ metabolic precursors of pyruvate as an electron donor, adding an amount of the selected electron donor equal to or in excess of an amount sufficient for reduction of an electron acceptor contaminant (e.g., uranium, or a nonaqueous halogenated solvent) to the groundwater or soil of a contaminated site. In certain embodiments, the electron donor is selected from the group consisting of lactic acid, salts thereof, lactate esters, poly-lactate, or mixtures thereof. In various embodiments, the *Geobacter* strain can be added before, after or during adding the selected electron donor or a combination thereof.

In some embodiments, a method of improved in situ bioremediation comprises using a *Geobacter* strain selected from a strain of *Geobacter sulfurreducens, Geobacter metallireducens, Geobacter lovleyi, Geobacter pickeringii, Geobacter grbiciae, Geobacter pelophilus, Geobacter bremensis, Geobacter hydrogenophilus, Geobacter uraniireducens, Geobacter humireducens, Geobacter bemidjiensis, Geobacter argillaceus, Geobacter chapellei, Geobacter psychrophilus, Geobacter pilgrimii, Geobacter plymouthensis, Geobacter rifilensis, Geobacter coloradoensis,* or a mixture thereof. In certain embodiments, the *Geobacter* strain is a *Geobacter sulfurreducens* strain.

Lactate is a convenient electron donor that can be added to the subsurface at a contaminated site to promote in situ bioremediation of a variety of bacterial species (e.g., uranium bioremediation, etc.). However lactate is not commonly found to be naturally present in anaerobic sedimentary environments where *Geobacter* species are usually the predominant microorganisms. Additionally, even when added to environment for improvement of bioremediation, although a wild type (ancestral) strain can use lactate, such use is not an efficient utilization of lactate as a carbon source and electron donor. Thus, lactate was a candidate for an adaptation study. Lactate is more electron dense than acetate, and is one of many precursors of pyruvate, which ancestral wild type strains are incapable of oxidizing. Sodium lactate is a convenient electron donor for in situ bioremediation applications. For example, poly-lactate, a time released form of sodium lactate, reduces the requirement of continuous pumping into a site and monitoring, both of which are necessary in cases of bioremediation promoted by other electron donors such as acetate.

In bioremediation applications where contaminants act as electron acceptors (e.g., reductive dechlorination, uranium reduction), a contaminant (e.g., chloroethene, uranium VI) acts as an electron acceptor. The process can be limited in the field by the availability of sufficient suitable electron donors. Additionally, bioremediation through reduction of contaminants can be totally or partially inhibited by the presence of competing inorganic electron acceptors (e.g., oxygen, nitrate, iron, and sulfate), as many oxidizable organic compounds potentially could make suitable electron donors. For an electron donor to be useful for enhanced in situ bioremediation, it is optimally safe to use, facilitates the desired reaction, be relatively inexpensive, and be utilized effectively by a microorganism as an electron donor. Lactate is a convenient electron donor having these properties, since it is innocuous enough for use in the food and medical industries, and has been demonstrated to facilitate reductive dechlorination of chlorinated solvents in several laboratory studies. Thus, use of lactate as an electron donor to facilitate reductive dechlorination is established, and has been applied primarily for remediation primarily in aqueous-phase contaminants, and more recently in non-aqueous-phase contaminants where the addition of high concentrations of a lactate solution has been shown to enhance mass transfer of nonaqueous contaminants such as chlorinated solvents, making them highly bioavailable. The use of microorganisms capable of efficient utilization of lactate as a carbon source and electron donor further improves such applications.

Facilitated transport and enhanced bioavailability of contaminants (e.g., uranium VI, nonaqueous chlorinated solvents) through addition of lactate or a derivative thereof as an electron donor and a microorganism capable of efficient utilization of lactate takes advantage of processes that have made natural attenuation and approaches to bioremediation so popular. Additionally, utilization of methods of adding lactate or a derivative thereof as an electron donor and a microorganism capable of efficient utilization of lactate or a derivative thereof significantly can significantly reduce contaminant source longevity by enhancing mass transfer from a contaminated site (e.g., facilitation of collection of insoluble uranium, transfer of chlorinated solvent to the aqueous phase). Capital costs associated with the approach are minimal, because a simple, potentially portable, injection/application system and monitoring of wells are required. Initial mass removal may be relatively slower than some other application technologies, however the approach is sustainable for a relatively low cost, and requires no extraction and treatment of contaminated soil or ground water except for routine monitoring, and as applicable, removal of precipitant uranium at a preferred localized site. Low capital cost, in situ contaminant destruction, unobtrusive appearance, public acceptance, low maintenance requirements, and the like, contribute to improved bioremediation application in source zone areas because, using this process, contaminant source longevity can be greatly reduced. Many of these advantages are not only beneficial to owners of contaminated sites, but also reduce risk of further releases of contaminants to the public and the environment.

Addition of high concentrations of lactate or a derivative thereof in conjunction with a microorganism capable of efficient utilization of lactate or a derivative thereof not only provide an electron donor to expedite reduction of contaminant (e.g., reduction of uranium VI, reductive dechlorination), but also facilitates mass transfer of the contaminant (e.g., precipitation of uranium IV at a localized site, transfer of nonaqueous chlorinated solvents into the aqueous phase) in a manner that makes resulting reduced contaminant products highly accessible for removal and/or bioavailable, resulting in facilitation of removal. Lactate has been proposed to also act as a surfactant or co-solvent that brings nonaqueous chlorinated solvents into solution. The intimate contact of contaminants in a site (e.g., uranium, chlorinated solvents) as electron acceptors with lactate as an electron donor in the presence of microorganism capable of facilitating reduction of the contaminant enhances bioavailability and leads to improved removal of contaminants and rapid biodegradation. Depletion of a residual contamination source can be potentially greatly accelerated due to the presence of microorganisms capable of efficient utilization of lactate. The use of lactate or a derivative thereof to facilitate transport of chlorinated solvents into the aqueous phase and dramatically increase their bioavailability opens up a wide range of applications for enhanced in situ bioremediation of chlorinated solvents present as nonaqueous phase liquids at residual saturation in ground water. The use of a relatively inexpensive compound that accomplishes removal of contaminants combines advantages of mass removal with those of enhanced bioremediation. Use of an adapted microorganism capable of efficient utilization of lactate and derivatives thereof in conjunction with bioremediation application methods therefore advances the efficiency of this process.

The most appropriate application of this process is to sites with residual contaminant (e.g., chlorinated solvent, uranium) in groundwater or soil source areas in the subsurface, comprising primarily contaminants at residual saturation. These are common at both federal and industrial facilities. When very large contaminant pools are present (e.g., uranium contaminated water, mobile DNAPL pools), mass transfer rates may be too slow to affect remediation in a reasonable time frame for effective removal or remediation; and more aggressive, capital-intensive approaches may be warranted.

The present invention is illustrated by the following examples, which should not be construed as further limiting. The contents of all references, pending and published patent applications and granted patents, cited throughout this application are hereby expressly incorporated by reference.

EXAMPLE 1

Generation of *Geobacter* Strains Capable of Efficient Utilization of Lactate

The ancestral (or wild type) strain of *G. sulfurreducens* is unable to utilize energy/electron-dense compounds, such as pyruvate, various sugars and glycerol (Caccavo, et al. 1994). However, genes required for glycolysis and glycerol oxidation as well as those required to convert pyruvate to acetyl-CoA are present in the *Geobacter sulfurreducens* genome (Methe, Nelson et al. 2003). Under normal laboratory conditions *G. sulfurreducens* is grown with acetate as an electron donor and fumarate as an electron acceptor. The average doubling time of a culture grown on acetate-fumarate media is about five hours. It was previously reported that *G. sulfurreducens* could not grow on media containing lactate as an electron donor. We have found, however, the strain does grow, though very slowly. The doubling time of the wild type strain PCA grown on lactate-fumarate media is greater or equal to 24 hours.

An adaptation study of selection for strains which could achieve faster growth using lactate as an electron donor, was performed using five parallel cultures prepared from a frozen stock of ancestral strain *Geobacter sulfurreducens* PCA (ATCC-51573). The ancestral strain was also the strain used for the original genome sequence of *Geobacter sulfurreducens* in 2002. Additional control stocks of the ancestral strain were also prepared for later growth curves and DNA extraction for sequence analysis. Cultures were grown in NB media (Coppi, M. V., et al. (2001). "Development of a genetic system for *Geobacter sulfurreducens*." Appl Environ Microbiol 67(7): 3180-7) with 10 mM lactic acid as an electron donor and 40 mM fumarate as an electron acceptor. Coppi et al. (2001) describe NBAF, a modified form of the medium contains 15 mM acetate as the electron donor and 40 mM fumarate as the electron acceptor. Its composition per liter of deionized water is 0.42 g of $KH_2PO_4$, 0.22 g of $K_2HPO_4$, 0.2 g of $NH_4Cl$, 0.38 g of KCl, 0.36 g of NaCl, 0.04 g of $CaCl_2.2H_2O$, 0.1 g of $MgSO_4.7H_2O$, 1.8 g of $NaHCO_3$, 0.5 g of $Na_2CO_3$, 2.04 g of $NaC_2H_3O_2.3H_2O$, 6.4 g of $Na_2C_4H_4O_4$, 0.5 ml of 0.1% resazurin, 1.0 ml of 100 mM $Na_2SeO_4$, 10.0 ml of a vitamin solution (Lovley, D. R., R. C. Greening, and J. G. Ferry. 1984. Rapidly growing rumen methanogenic organism that synthesizes coenzyme M and has a high affinity for formate. Appl. Environ. Microbiol. 48:81-87), and 10.0 ml of NB trace mineral solution. The composition of the NB trace mineral solution per liter of deionized water is 2.14 g of nitriloacetic acid, 0.1 g of $MnCl_2.4H_2O$, 0.3 g of $FeSO_4.7H_2O$, 0.17 g of $CoCl_2.6H_2O$, 0.2 g of $ZnSO_4.7H_2O$, 0.3 g of $CuCl_2.2H_2O$, 0.005 g of $AlK(SO_4)_2.12H_2O$, 0.005 g of $H_3BO_3$, 0.09 g of $Na_2MoO_4$, 11 g of $NiSO_4.6H_2O$, and 0.2 g of $Na_2WO_4.2H_2O$. Determination of doubling times was done using NB medium having the indicated electron donor, but having ferric chloride instead of fumarate as an electron acceptor. See also U.S. published patent application US2008/028664, which is incorporated herein in its entirety.

Cultures were grown in pressure tubes with 10 ml of media, gassed with 80:20 mix of $N_2:CO_2$, sealed with rubber stoppers, and grown at 30° C. (Lovley and Phillips 1988). In order to select for faster growth on lactate, the growth of the cultures was continually monitored and an aliquot always transferred in mid to late exponential phase to a new pressure tube containing fresh media. Transfers were performed anaerobically and each inoculum was 1/100 of the total 10 ml volume. Five parallel cultures of *G. sulfurreducens* were adapted for faster growth on lactate by repeated serial transfers of aliquots of mid/late-exponential phase cultures for over 500 generations. FIG. 1 depicts the growth rates of cultures in NB lactate-fumarate growth medium that were repeatedly passaged to produce strains that could use lactate efficiently as an electron donor. The curves represent five parallel cultures that were continuously transferred in NB lactate medium. The growth rate per hour (ordinate) is plotted against the transfer number (abscissa).

After 500 generations, lactate-adapted strains have a doubling time in NB lactate ferric chloride media of approximately 5 hours, which is similar to the doubling time of the ancestral strain grown in NB media containing acetate. At each transfer, colonies were either frozen for maintenance of adapted isolate strains, or transferred to fresh media for further adaptation. The adapted strains of *Geobacter sulfurreducens* were isolated from cultures for further characterization at transfer number 23 (isolate 1-23, which had been grown on NB lactate-fumarate growth medium for 150 generations), and at transfer number 50 (isolate 1-50, also called strain ZMS-153, which had been grown on lactate for 330 generations).

EXAMPLE 2

Phenotypic Characterization of Lactate Adapted Strains

Isolate 1-23 and isolate 1-50 were then compared to the ancestral strain for growth characteristics on lactate and acetate. Isolate 1-50, which had been grown on lactate for 330 generations, had a doubling time of 5 hours on NB lactate medium and 9.8 hours on NB acetate medium. An evolutionary tradeoff seemed to occur due to the prolonged exposure on lactate of isolate 1-50, resulting in increased fitness on lactate and some loss of fitness on acetate. Isolate 1-23, which had been grown on lactate for 150 generations, had increased fitness on NB lactate medium with a doubling time of 6 hours, and only a slight decrease in fitness on NB acetate medium with a doubling time of 6 hours.

Figure 2:
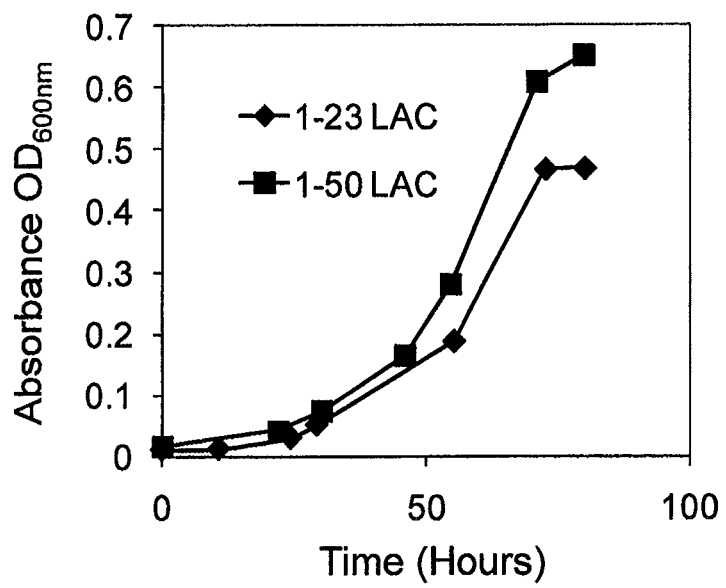
FIG. 2 depicts growth curves over time of lactate-adapted strains isolate 1-23 (filed diamonds) and isolate 1-50 (filled squares) strains grown in NB medium containing 10 mM lactate as an electron donor and 40 mM fumarate as an electron acceptor. The strain that was adapted longer to the lactate medium, isolate 1-50, showed a faster growth rate than isolate 1-23.

FIG. 2 depicts growth curves over time of the lactate-adapted isolate 1-23 strain (filed diamonds) and the isolate 1-50 strain (ZMS-153, filled squares) grown in NB medium containing 10 mM lactate as an electron donor and 40 mM fumarate as an electron acceptor. The strain that was adapted longer to the lactate medium, isolate 1-50, showed a faster growth rate in the NB lactate medium than isolate 1-23.

Figure 3:
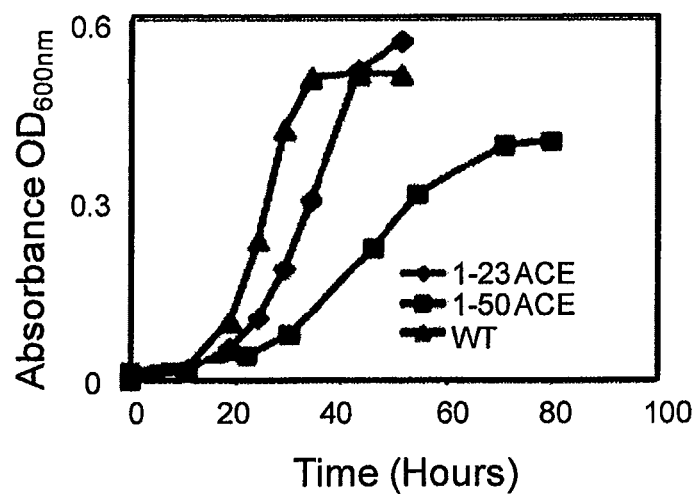
FIG. 3 depicts growth curves over time of a wild-type ancestral strain (WT, filled triangles), and lactate-adapted strains, isolate 1-23 (filed diamonds) and isolate 1-50 (filled squares) strains grown in NBAF medium containing 10 mM acetate and 40 mM fumarate. The strain that had a faster growth rate in the NB lactate medium, isolate 1-50, showed a slower growth rate in acetate medium than isolate 1-23.

FIG. 3 depicts growth curves over time of a wild-type ancestral strain (WT, filled triangles), and lactate-adapted strains, isolate 1-23 (filed diamonds) and isolate 1-50 (filled squares) grown in NBAF medium containing 10 mM acetate and 40 mM fumarate. The strain that had a faster growth rate in the NB lactate medium, isolate 1-50, showed a slower growth rate in acetate medium than isolate 1-23.

Isolate 23 and isolate 50 were also compared to the ancestral strain for growth on additional substrates. Isolate 23 has the ability to grow and utilize a diverse range of substrates that both the ancestral strain and isolate 50 are unable to utilize. For example, isolate 23 has gained the ability to grow by oxidization of pyruvate, glycerol, glucose and xylose.

EXAMPLE 3

Genomic Characterization of Lactate Adapted Strains

Sequencing of the 3.5 MB genome of each of isolate 1-23, isolate 1-50 (ZMS-153), and strains ZMS-253, ZMS-353 and ZMS-453, described below, was carried out to identify changes that had occurred on the genome level. The resulting sequences were compared to the known sequence of the ancestral strain, as well as compared to control sequencing carried out in parallel on the ancestral strain.

A mutation located in the open reading frame of GSU0514 (SNP 548250 G-A (E-K)), resulting in a glutamate to lysine change in the protein sequence was identified in all the strains that had been adapted to lactate, i.e., 1-23, ZMS-153, ZMS-253, ZMS-353 and ZMS-453. All strains showed a single nucleotide pair (SNP) mutation of G to A at position 548250 in GSU0514 that results in an E to K change in the gene product, a repressor of succinyl-CoA synthetase.

GSU0514 is a transcriptional repressor. DNA binding assays indicate that the repressor acts on the succinyl-CoA synthetase (SUCOAS) promoter, inhibiting transcription of that gene in the ancestral strain while grown on acetate-fumarate media. This finding is supported by enzyme assays as well, since under acetate-fumarate growth conditions, no succinyl-CoA synthetase activity was detected in the ancestral wild type strains.

Figure 4:
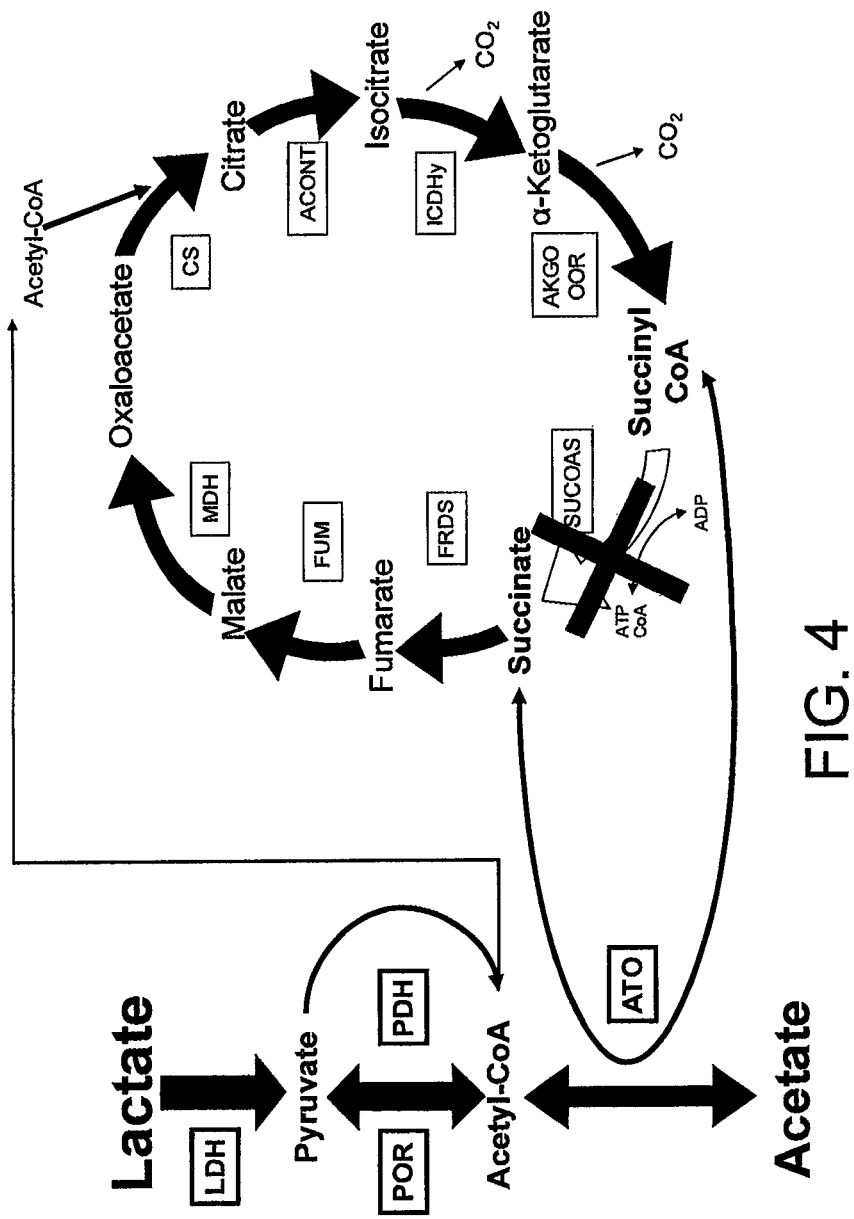
FIG. 4 depicts the proposed alternate pathway for the production of succinate and oxidation of acetate in ancestral wild-type *Geobacter* species, indicating repression of the enzyme succinyl-CoA synthetase.

Because succinyl-CoA synthetase is an important enzyme of the tricarboxylic acid (TCA) cycle for generation of succinate, Geobacter (e.g., G. sulfurreducens) evolved in the environment to develop another path for production of succinate: utilizing the coupled reaction of Acetate+Succinyl-CoA→Acetyl-CoA+Succinate. The acetyl-CoA transferase (ATO) enzyme carries out this reaction as a detour out of the TCA cycle. FIG. 4 depicts the proposed alternate pathway for the production of succinate and oxidation of acetate in ancestral wild-type Geobacter species, indicating repression of the enzyme succinyl-CoA synthetase.

Microarray experiments were carried out to identify whether adapted strains demonstrated increased levels of transcription of succinyl-CoA synthetase. These experiments confirmed that adapted strains have increased succinyl-CoA synthetase expression as compared to ancestral strains.

Mutagenesis. To reproduce the phenotype of the lactate adapted strain into the wild-type, the mutant GSU0514 gene from the lactate adapted strain was inserted into the genome of the wild type using the Cre-Lox system (Marx, C. J.; Lidstrom, M. E., Broad-host-range cre-lox system for antibiotic marker recycling in gram-negative bacteria. BioTechniques 2002; 33(5):1062-7). The plasmid pZS was digested with NheI, gel-purified, and used to clone the XbaI fragment (gentamicin resistance cassette flanked with two LoxP sites) from the plasmid pUC::GmRLoxP. The new recombinant plasmid (pWA4) was digested with EcoRI and the resulting mutagenic fragment (2332 bp) was gel-purified and ethanol-precipitated. Then, 2 µl (0.8 µg DNA) were used to transform electrocompetent cells of the GSU0514 knock-out strain. After electroporation, the cells were recovered for 18 h in reduced NBLF media containing 0.1% yeast extract. Preparation of electrocompetent cells and electroporation were performed as described (Coppi, Leang et al. 2001). The knock-in mutants were selected by plating samples from the recovery tube on NBAF-Gm (20 µg ml$^{-1}$). Mutants from the Gm plates were purified once on selective plates and then inoculated into NBLF-Kan tubes to test for the loss of the Kan$^r$. Kan sensitive colonies were checked by PCR to confirm the insertion of the mutagenic fragment into the chromosome.

Locus specific primers (GSU0514F, tgtctcctcctgaaaata-gaac (SEQ ID NO:1); and GSU0514R, gggcttttctgctagcgat-gaaagccgagcttcatg (SEQ ID NO:2) and the following conditions were used: 94° C. for 1 min followed by 30 cycles of 94° C. for 30 sec; 65° C. for 45 sec; 72° C. for 90 sec, and finally 72° C. for 10 min. To evict the Gm$^r$ cassette, electrocompetent cells of the knock-in mutant were transformed with pCM158 expressing the Cre-recombinase gene. After electroporation, transformants were recovered overnight in reduced NBLF tubes containing 0.1% yeast extract. Samples from the recovery tube were plated onto NBLF-Kan (200 µg ml$^{-1}$). Kan$^r$ mutants were purified twice nonselectively and then tested for the loss of the Kan$^r$ and Gm$^r$ cassettes in reduced NBLF tubes. All incubations were at 30° C. and the NBLF plates were incubated in the glove bag. Mutations were confirmed by sequencing and LA Taq DNA polymerase from Takara was used for the PCR.

Figure 5:
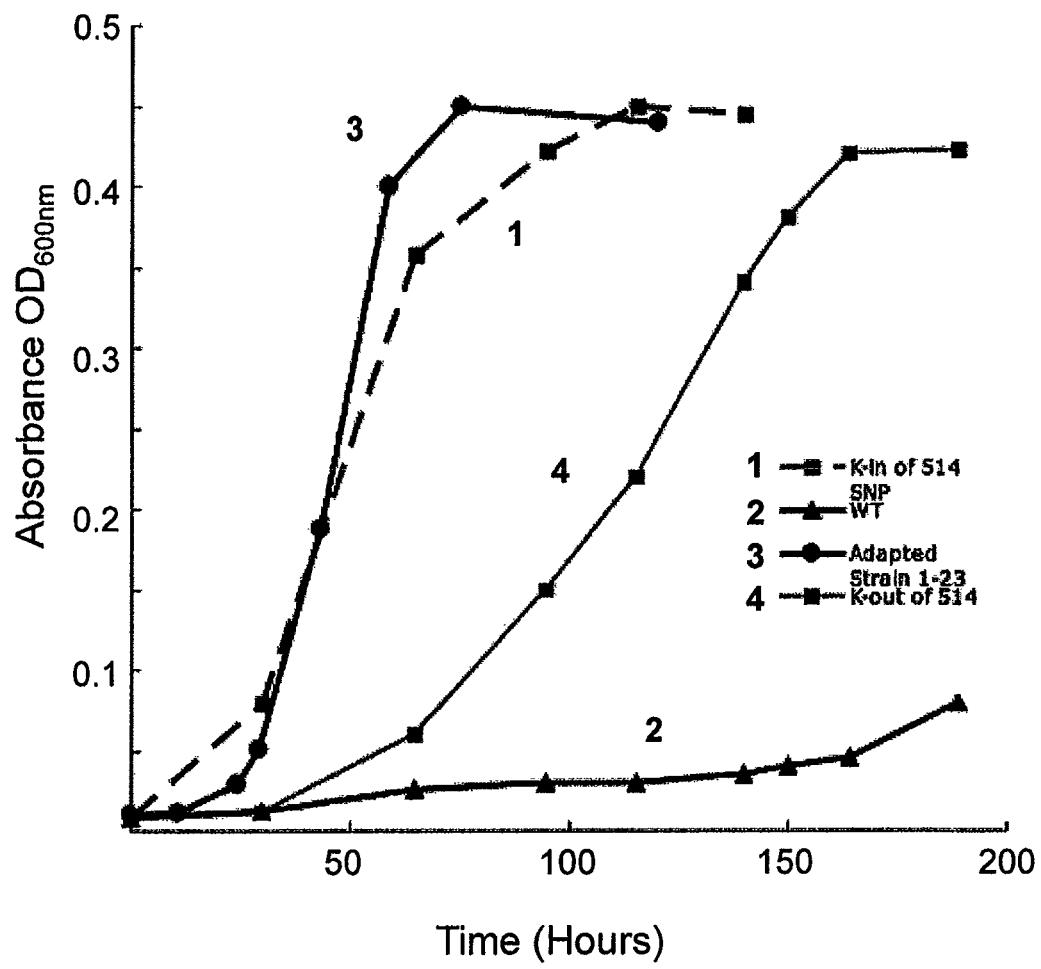
FIG. 5 shows the results of knock-out and knock-in studies, showing the growth rates on NB lactate medium of the wild type strain (WT, filled triangles, curve 2), the lactate adapted strain 1-23 (filled circles, curve 3), a strain in which the mutant GSU0514 gene from the lactate adapted strain was inserted into the genome of the wild type using the Cre-Lox system ("K-in of 514 SNP," filled squares and dashed line, curve 1), and a strain in which the mutant GSU0514 gene was "knocked out" of the genome of the lactate adapted strain ("K-out of 514 SNP," filled squares and continuous line, curve 4). Introduction of the mutant GSU0514 gene from the lactate adapted strain into the wild type gene essentially reproduces the ability of the lactate adapted strain 1-23 to grow in NB lactate medium (cf. curves 1 and 3). Conversely, the knock-out strain is reduced in the ability to grow in NB lactate medium (cf. curves 4 and 3).

FIG. 5 shows the results of knock-out and knock-in studies, showing the growth rates on NB lactate medium of the wild type strain (WT, filled triangles, curve 2), the lactate adapted strain 1-23 (filled circles, curve 3), a strain in which the mutant GSU0514 gene from the lactate adapted strain was inserted into the genome of the wild type using the Cre-Lox system ("K-in of 514 SNP," filled squares and dashed line, curve 1), and a strain in which the mutant GSU0514 gene was "knocked out" of the genome of the lactate adapted strain ("K-out of 514 SNP," filled squares and continuous line, curve 4). Introduction of the mutant GSU0514 gene from the lactate adapted strain into the wild type gene essentially reproduces the ability of the lactate adapted strain 1-23 to grow in NB lactate medium (cf. curves 1 and 3). Conversely, the knock-out strain is reduced in the ability to grow in NB lactate medium (cf. curves 4 and 3).

EXAMPLE 4

Use of the Citric-Acid Cycle in Lactate-Adapted Strains

Growth on NB lactate medium involves a different scenario than that described above in Example 3. When acetate is not present to drive the coupled reaction of the ATO enzyme, succinate is still produced in lactate-adapted strains under lactate-fumarate growth conditions, as evidenced by enzyme assays carried out using whole cell extracts of both isolates 1-23 and 1-50, as well as in the wild-type ancestral strain. The results were consistent with the genomic data, suggesting that mutation in either the repressor of expression or the gene encoding the succinyl Co-A synthetase (SUCOAS) enzyme are affecting the activity and ability of the adapted strain to utilize lactate. While not being held to a particular mechanism, it is our understanding from the combination of experiments that the SUCOAS enzyme is now unrepressed and able to be expressed. This is evidence that for the first time that the TCA cycle of *Geobacter sulfurreducens* is complete and active.

Figure 6:
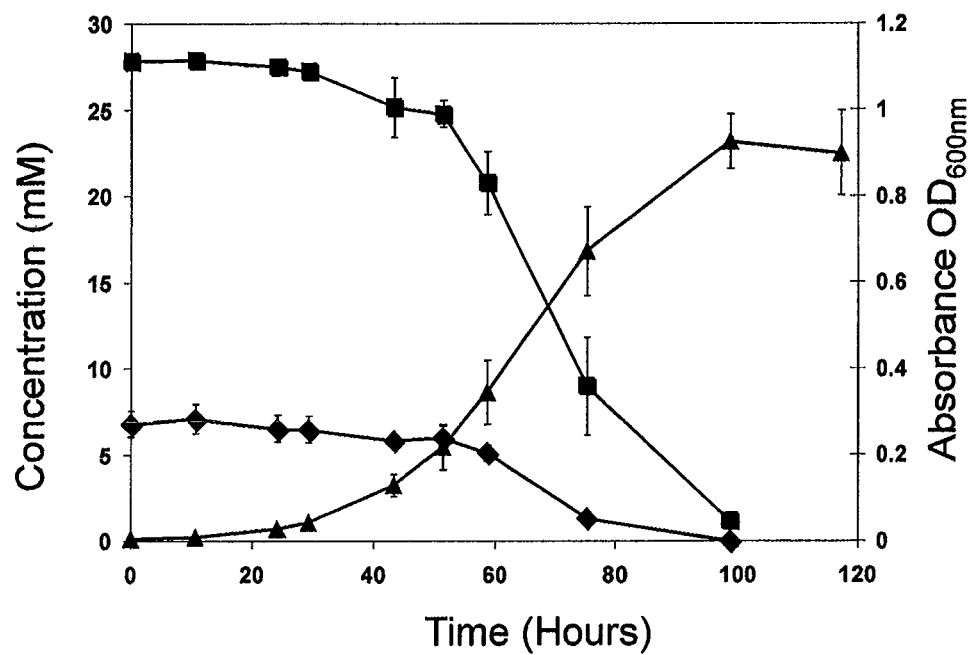
FIG. 6 shows the results of studies of the ability of the lactate adapted strain 1-23 to grow in NB medium containing 10 mM pyruvate. The data plotted are the average of three replicates±one standard deviation. The growth curve (filled triangles) shows slower growth on pyruvate than was observed on lactate (cf.

FIG. 6 shows the results of studies of the ability of the lactate adapted strain 1-23 to grow in NB medium containing 10 mM pyruvate. The data plotted are the average of three replicates±one standard deviation. The growth curve (filled triangles) shows slower growth on pyruvate than was observed on lactate (cf. FIG. 2). Also plotted are the changes in the concentrations of pyruvate (filled diamonds) and fumarate (filled squares) in the medium, as determined by HPLC.

The characteristics of the strains developed in this studies compared to the characteristics of the wild type strain are summarized in Table 1, below.

EXAMPLE 5

Additional Phenotypic Characterization of Strains Using Enzyme Assays

There are other ways to study the metabolism of *G. sulfurreducens* using adapted strains described herein. Additional enzyme assays could provide insight into each specific reaction of the TCA cycle by comparing activities of the different strains under various growth conditions. Enzymes of the TCA cycle could have differences between strains, and/or when grown under various growth conditions. Enzyme assays include, but are not limited to: lactate dehydrogenase, pyruvate oxidoreductase, pyruvate dehydrogenase, acetyl-CoA transferase, citrate synthase, aconitase, isocitrate dehydrogenase, α-ketoglutarate dehydrogenase, fumarate reductase, fumarase, and malate dehydrogenase. These enzymes and assays are well known in the art and assays are readily available and known to those skilled in the art. Strains can be grown under desired conditions, and may include growth under generic growth media or under specified conditions for a particular enzyme assay, as applicable and known in the art, and the strains are harvested for assays as applicable to a particular enzyme.

EXAMPLE 6

Comparison of Biomass Yield and Energy Maintenance of Adapted Strains

An additional way of exploring physiological differences among adapted strains and the ancestral wild type is to compare biomass yields as well as maintenance energies of strains on different electron donors. The lactate specialist ZMS-153

TABLE 1

Summary Table of Strains

| Strain | Derived From Strain | Adapted to electron donor | ATCC Deposit No. | Doubling time NB growth medium, ferric chloride as electron acceptor, hours | | | | |
|---|---|---|---|---|---|---|---|---|
| | | | | acetate | lactate | glucose | xylose | glycerol |
| PCA | PCA | 15 mM acetate | ATCC-51573 | 5 | >24 | | | |
| Isolate 1-23 Example 1: 150 generations | PCA | 10 mM lactate | | 6 | 6 | | | |
| ZMS-153 (isolate 1-50) Example 1: 330 generations | PCA | 10 mM lactate | PTA-10249 | 9.8 | 5 | | | |
| ZMS-253 Example 7: 45 generations | 1-23 | 2.5 mM glucose | PTA-10250 | | | 21 | | |
| ZMS-453 Example 8: 110 generations | 1-23 | 5 mM xylose | | | | | 20 | |
| ZMS-353 Example 9: 160 generations | 1-23 | 5 mM glycerol | | | | | | 15 |

Figure 7:
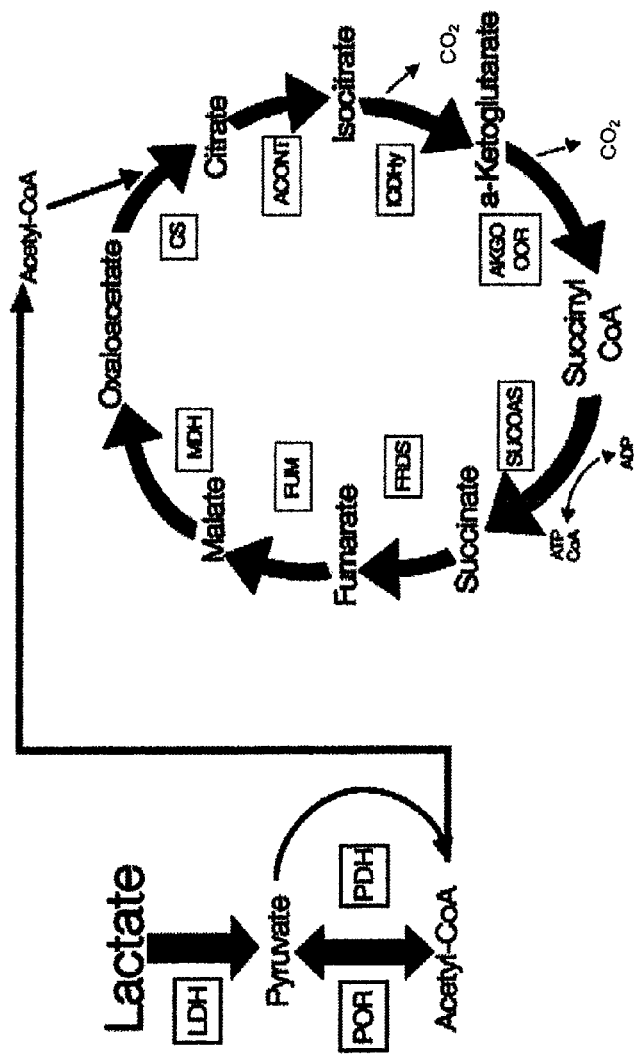
FIG. 7 illustrates the proposed pathway for production of succinate and oxidation of lactate in *Geobacter* species evolutionarily adapted to efficiently utilize lactate.

FIG. 7 illustrates the proposed pathway for production of succinate and oxidation of lactate in *Geobacter* species evolutionarily adapted to efficiently utilize lactate.

would be expected to have a greater yield of biomass and maintenance energy when grown in lactate than that of the ancestral strain, due to its continued adaptation on lactate.

For example, biomass yield and maintenance energy can be tested using continuous culture devices (e.g., chemostats). Chemostats comprise a sterile media reservoir that is added drop-wise to a growth vessel at a constant rate, while at the same time spent medium leaves the culture at that same rate and is collected in a waste reservoir. A peristaltic pump regulates the flow rate in the chemostat to keep it kept constant, which controls the growth rate of the culture. One essential nutrient is limiting, to control the biomass yield. To test for utilization of an electron donor, for example, the electron donor (e.g., lactate) is limiting in the system. Methods known to those skilled in the art have been developed that allow chemostat experiments using anaerobic microorganisms.

EXAMPLE 7

Generation of *Geobacter* Strains Capable of Efficient Utilization of Glucose

Further studies were undertaken with the isolate 1-23 strain to increase the growth and the efficiency of utilization of glucose as an electron donor. The selection for strains that could achieve faster growth using glucose as an electron donor was performed using five separate parallel cultures prepared from a frozen stock of isolate 1-23 strain *Geobacter sulfurreducens* (preparation described above in Example 1). Cultures were grown in NB media with the lactate replaced by 2.5 mM glucose as an electron donor and 40 mM fumarate as an electron acceptor. Cultures were grown in pressure tubes, culture growth monitored and aliquots inoculated into tubes containing sterile NB growth medium, as described above in Example 1. At each transfer, colonies were frozen for maintenance and/or transferred to fresh media for adaptation of strains.

Figure 8:
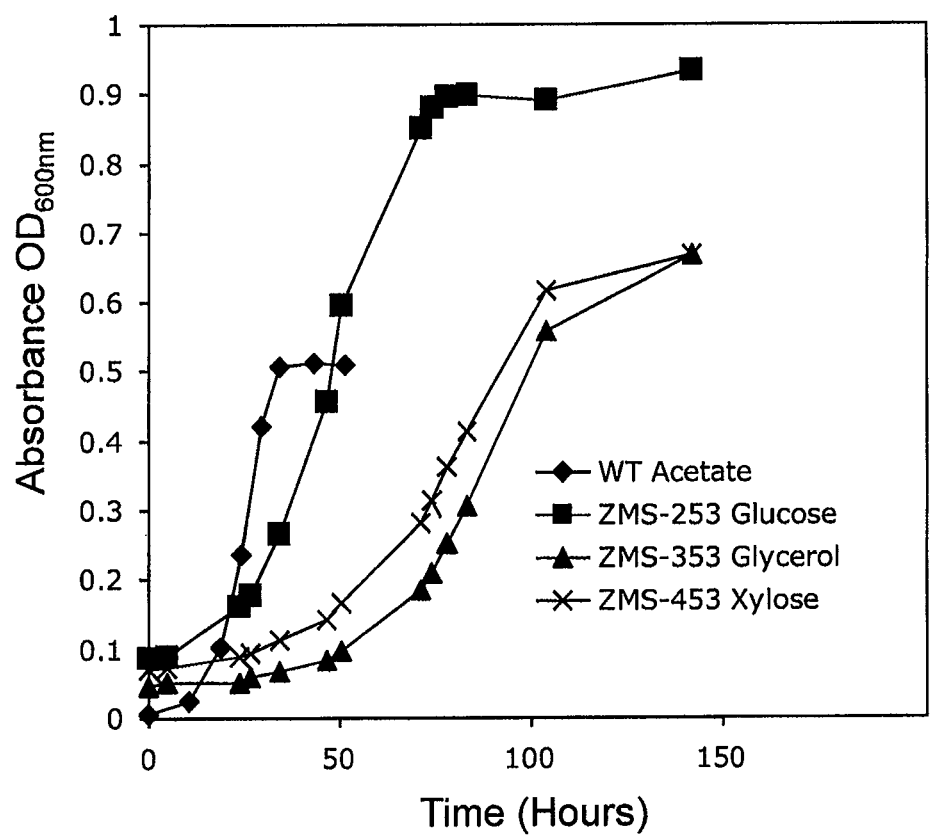
FIG. 8 compares the growth curves over time of strains ZMS-253 (adapted to NBFC medium containing 2.5 mM glucose, filled squares), ZMS-353 (adapted to NBFC medium containing 5 mM glycerol, filled triangles), and ZMS-453 (adapted to NBFC medium containing 5 mM xylose, "X") to the growth curve of the wild type strain (filled diamonds) grown in NBAF medium.

FIG. 8 compares the growth curves over time of strains ZMS-253 (adapted to NBFC medium containing 2.5 mM glucose, filled squares), ZMS-353 (adapted to NBFC medium containing 5 mM glycerol, filled triangles), and ZMS-453 (adapted to NBFC medium containing 5 mM xylose, "X") to the growth curve of the wild type strain (filled diamonds) grown in NBAF medium.

Cultures of *G. sulfurreducens* strain 1-23 adapted for faster growth on glucose by repeated serial transfers of cultures showed increased growth rates in the NB glucose medium with successive transfers. For example, for the culture produced by the $4^{th}$ transfer in NB glucose medium, the exponential phase started at about 488 hours after inoculation. For the culture produced by the $5^{th}$ transfer in NB glucose medium, the exponential phase started at about 200 hours after inoculation, but the exponential phase of the culture produced by the $8^{th}$ transfer started at about 120 hours after inoculation. The time to the start of the exponential phase of the culture produced by the $5^{th}$ transfer was about 41% of the same time period in the preceding culture, but time period the start of the exponential phase of the culture produced by the $8^{th}$ transfer was about 60% of the same time period for culture produced by the $5^{th}$ transfer. Thus, while growth rates tended to increase with subsequent transfers, the rate of increase in the growth rate tended to decline after a while. A similar trend can be seen from transfers 1-23 in FIG. 1.

An isolate selected after 29 transfers (approximately 45 generations), ZMS-253, had an estimated doubling time of about 21 hours in NB medium containing 2.5 mM glucose with ferric chloride as an electron acceptor. Genetic analysis (described above in Example 3) of the ZMS-253 strain showed a single nucleotide pair (SNP) mutation of G to A at position 548250 in GSU0514 that results in an E to K change in the gene product.

EXAMPLE 8

Generation of *Geobacter* Strains Capable of Efficient Utilization of Xylose

Further studies were undertaken with the isolate 1-23 strain to increase the growth and the efficiency of utilization of xylose as an electron donor. The selection for strains that could achieve faster growth using xylose as an electron donor was performed using five separate parallel cultures prepared from a frozen stock of isolate 1-23 strain *Geobacter sulfurreducens* (preparation described above in Example 1). Cultures were grown in NB media with the lactate replaced by 5 mM xylose as an electron donor and 40 mM fumarate as an electron acceptor. Cultures were grown in pressure tubes, culture growth monitored and aliquots inoculated into tubes containing sterile NB growth medium, as described above in Example 1. At each transfer, colonies were frozen for maintenance and/or transferred to fresh media for adaptation of strains.

Cultures of *G. sulfurreducens* adapted for faster growth in media containing 5 mM xylose by repeated serial transfers of cultures were isolated after 18 transfers (approximately 110 generations). See FIG. 8. The resulting isolate, ZMS-453, had an estimated doubling time of about 20 hours in NB medium with ferric chloride as an electron acceptor instead of fumarate, and containing 5 mM xylose. Genetic analysis (described above in Example 3) of the ZMS-453 strain showed a single nucleotide pair (SNP) mutation of G to A at position 548250 in GSU0514 that results in an E to K change in the gene product.

EXAMPLE 9

Generation of *Geobacter* Strains Capable of Efficient Utilization of Glycerol

Further studies were undertaken with the isolate 1-23 strain to increase the growth and the efficiency of utilization of glycerol as an electron donor. An adaptation study of selection for strains which could achieve faster growth using glycerol as an electron donor, was performed using parallel cultures prepared from a the adapted isolate 23 strain *Geobacter sulfurreducens*. Cultures were grown in NB media with 5 mM glycerol as an electron donor and 40 mM fumarate as an electron acceptor. Cultures were grown in pressure tubes, culture growth monitored and aliquots inoculated into tubes containing sterile NB growth medium, as described above in Example 1. At each transfer, colonies were frozen for maintenance and/or transferred to fresh media for adaptation of strains.

Cultures of *G. sulfurreducens* strain 1-23 adapted for faster growth on glycerol by repeated serial transfers of cultures showed increased growth rates in the NB glycerol medium with successive transfers. For example, for the culture produced by the $4^{th}$ transfer in NB glycerol medium, the exponential phase started at about 400 hours after inoculation. For the culture produced by the $5^{th}$ transfer in NB glycerol medium, the exponential phase started at about 88 hours after inoculation, and the exponential phase of the culture produced by the $8^{th}$ transfer started at about 120 hours after inoculation. The time to the start of the exponential phase of the culture produced by the $5^{th}$ transfer was about 22% of the same time period in the preceding culture, but time period the start of the exponential phase of the culture produced by the 8th transfer was about 140% of the same time period for culture produced by the 5th transfer.

Cultures of *G. sulfurreducens* adapted for faster growth on 5 mM glycerol by repeated serial transfers of cultures were isolated after 26 transfers (approximately 160 generations). See FIG. 8. The resulting isolate, ZMS-353, had an estimated doubling time of about 15 hours in NB medium with ferric chloride as an electron acceptor instead of fumarate, and containing 5 mM glycerol. Genetic analysis (described above in Example 3) of the ZMS-353 strain showed a single nucleotide pair (SNP) mutation of G to A at position 548250 in GSU0514 that results in an E to K change in the gene product.

EXAMPLE 10

Deposits of *Geobacter* Strains

The isolated *Geobacter sulfurreducens* strain adapted for utilizing and oxidizing glucose was deposited on Aug. 5, 2009, on behalf of University of Massachusetts, 225 Franklin Street, Boston, Mass. 02110, U.S.A., at the American Type Culture Collection, Patent Depository, 10801 University Boulevard, Manassas, Va. 20110, U.S.A., under Accession No. PTA-10250 (ZMS-253). The deposit has been made pursuant to, and in satisfaction of, the requirements of the Budapest Treaty on the International Recognition of the Deposit of Microorganisms for the Purposes of Patent Procedure.

The isolated *Geobacter sulfurreducens* strain adapted for utilizing and oxidizing lactate was deposited on Aug. 5, 2009, on behalf of University of Massachusetts, 225 Franklin Street, Boston, Mass. 02110, U.S.A., at the American Type Culture Collection, Patent Depository, 10801 University Boulevard, Manassas, Va. 20110, U.S.A., under Accession No. PTA-10249 (ZMS-153). The deposit has been made pursuant to, and in satisfaction of, the requirements of the Budapest Treaty on the International Recognition of the Deposit of Microorganisms for the Purposes of Patent Procedure.

While the foregoing invention has been described in some detail for purposes of clarity and understanding, these particular embodiments are to be considered as illustrative and not restrictive. It will be appreciated by one skilled in the art from a reading of this disclosure that various changes in form and detail can be made without departing from the true scope of the invention, which is to be defined by the appended claims rather than by the specific embodiments.

Patent and scientific literature referred to herein establishes knowledge that is available to those with skill in the art. Unless otherwise defined, all technical and scientific terms used herein have the same meaning as commonly understood by one of ordinary skill in the art to which this invention belongs. The issued patents, applications, and references that are cited herein are hereby incorporated by reference to the same extent as if each was specifically and individually indicated to be incorporated by reference. In the case of inconsistencies, the present disclosure, including definitions, will control.

What is claimed is:

1. A method of making an isolated adapted strain of an electricigenic microbe that can use an alternative organic compound as an electron donor wherein the alternative organic compound is not preferably used as an electron donor by a parent strain of the electricigenic microbe, comprising the steps of:
   a. providing a first vessel that contains a first culture, the first culture comprising the parent strain of the electricigenic microbe, wherein the parent strain is *Geobacter sulfurreducens* strain identified as ATCC deposit ATCC-51573, and
   a first growth medium that includes
   a preferred organic compound as an electron donor and
   a corresponding electron acceptor;
   b. setting n =1, where n is an integer from 1 to 100, inclusive;
   c. removing an aliquot of the parent strain of the electricigenic microbe after a growth interval;
   d. inoculating a second vessel that contains
   a second growth medium that includes
   an alternative organic compound that replaces the preferred organic compound as an electron donor and
   a corresponding electron acceptor
   with said aliquot of the parent strain of the electricigenic microbe to form an adapted culture;
   e. incrementing n by 1 according to the relation n =n +1;
   f. transferring an aliquot of the (n−1)th adapted culture to another vessel that contains the second growth medium to inoculate an nth adapted culture;
   g. monitoring the growth rate of the nth adapted culture, noting the start of an exponential phase, and continuing until the growth rate is in mid or late exponential phase;
   h. repeating steps d-g unless
   either the time period from inoculation until the start of the exponential phase of the nth adapted culture is more than 0.4 times the time period from inoculation until the start of the exponential phase of the (n−1)th adapted culture; or
   the increase in the growth rate of the nth adapted culture compared to its predecessor is less than that of the (n−1)th adapted culture compared to its predecessor, or
   the doubling time of the nth adapted culture in the second growth medium is greater than or equal to the doubling time of the parent strain in the first growth medium; and
   i. isolating the adapted strain of the electricigenic microbe from the nth adapted culture, wherein the adapted strain is *Geobacter sulfurreducens* strain identified as ATCC deposit PTA-10250.

2. The method of claim 1 wherein the preferred organic compound is acetate and the alternative organic compound is pyruvate or a $C_3$ to $C_{12}$ metabolic precursor of pyruvate.

3. The method of claim 1 wherein the preferred organic compound is acetate and the alternative organic compound is lactate.

4. The method of claim 1 wherein the preferred organic compound is lactate and the alternative organic compound is glucose.

5. The method of claim 4 wherein the adapted strain of *Geobacter sulfurreducens* is the strain identified as ATCC deposit PTA-10250.

6. The method of claim 1 wherein, the preferred organic compound is lactate and the alternative organic compound is glycerol.

7. The method of claim 6 wherein the adapted strain of *Geobacter sulfurreducens* is the strain identified as ATCC deposit PTA-10250.

8. The method of claim 1 wherein the preferred organic compound is lactate and the alternative organic compound is xylose.

* * * * *